United States Patent [19]

Morton, Jr.

[11] 4,365,075

[45] Dec. 21, 1982

[54] ω-ARYL-PGD COMPOUNDS

[75] Inventor: Douglas R. Morton, Jr., Portage, Mich.

[73] Assignee: The Upjohn Company, Kalamazoo, Mich.

[21] Appl. No.: 756,100

[22] Filed: Dec. 30, 1976

Related U.S. Application Data

[62] Division of Ser. No. 614,242, Sep. 17, 1975, Pat. No. 4,016,184.

[51] Int. Cl.² ............................................. C07C 69/76
[52] U.S. Cl. ......................................... 560/51; 560/53
[58] Field of Search ........................ 260/473 R, 473 G

[56]         References Cited
    FOREIGN PATENT DOCUMENTS 48-30848  7/1973  Japan ............................ 260/473 R
    7301094   7/1973  Netherlands .................... 260/473 R

*Primary Examiner*—Paul J. Killos
*Attorney, Agent, or Firm*—Robert A. Armitage

[57]            ABSTRACT

Prostaglandin analogs with the following cyclopentane ring structure:

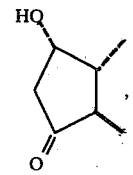

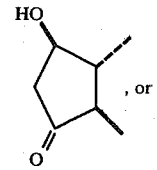

, or

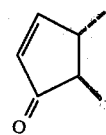

are disclosed along with intermediates useful in their preparation and processes for their preparation. These analogs are useful for the same pharmacological purposes as the prostaglandins, particularly and especially as blood platelet aggregation inhibitors.

142 Claims, No Drawings

ω-ARYL-PGD COMPOUNDS

The present application is a divisional application of Ser. No. 614,242, filed Sept. 17, 1975, now issued as U.S. Pat. No. 4,016,184, on Apr. 5, 1977.

The present invention relates to prostaglandin analogs for which the essential material constituting a disclosure therefor is incorporated by reference here from U.S. Pat. No. 4,016,184, issued Apr. 5, 1977.

I claim:

1. A prostaglandin analog of the formula

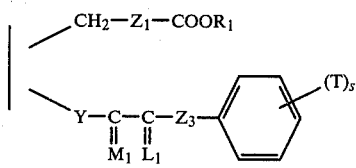

wherein D is

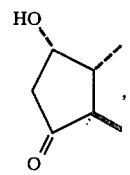

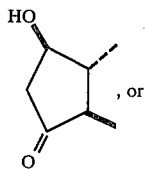

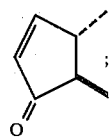

wherein Y is cis-CH=CH—, trans-CH=CH—, or —CH$_2$CH$_2$—; wherein Z$_1$ is 1. cis-CH=CH—CH$_2$—(CH$_2$)$_g$—CF$_2$—,
2. cis-CH=CH—CH$_2$—(CH$_2$)$_g$—CH$_2$,
3. cis-CH$_2$—CH=CH—(CH$_2$)$_g$—CH$_2$—,
4. —(CH$_2$)$_3$—(CH$_2$)$_g$—CF$_2$—,
5. —(CH$_2$)$_3$—(CH$_2$)$_g$—CH$_2$—,
6. —CH$_2$—O—CH$_2$—(CH$_2$)$_g$—CH$_2$—,
7. —(CH$_2$)$_2$—O—(CH$_2$)$_g$—CH$_2$—,
8. —(CH$_2$)$_3$—O—(CH$_2$)$_g$—, (9) 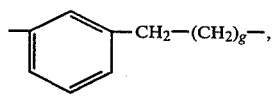

or

(10) 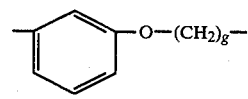

wherein g is one, 2, or 3; wherein M$_1$ is

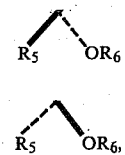

5 or

wherein R$_5$ and R$_6$ are hydrogen or methyl, with the proviso that one of R$_5$ and R$_6$ is methyl only when the other is hydrogen;

wherein L$_1$ is

or a mixture of

and

wherein R$_3$ and R$_4$ are hydrogen, methyl, or fluoro, being the same or different, with the proviso that one of R$_3$ and R$_4$ is fluoro only when the other is hydrogen or fluoro;

wherein Z$_3$ is oxa or methylene;

wherein T is chloro, fluoro, trifluoromethyl, alkyl of 1 to 3 carbon atoms, inclusive, or alkoxy of 1 to 3 carbon atoms, inclusive, and s is 0, 1, 2, or 3, the various T's being the same or different, with the proviso that not more than two T's are other than alkyl, with the further proviso that Z$_3$ is oxa only when R$_3$ and R$_4$ are hydrogen or methyl, being the same or different; and wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation; with the further proviso that D is

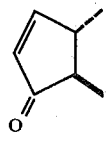

only when Y is cis- or trans-CH=CH—.

2. A compound according to claim 1, wherein D is

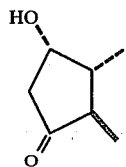

3. A compound according to claim 2, wherein $M_1$ is

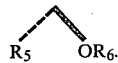

4. A compound according to claim 2, wherein $M_1$ is

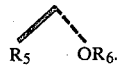

5. A compound according to claim 4, wherein Y is —$CH_2CH_2$—.

6. A compound according to claim 5, wherein $Z_3$ is methylene.

7. A compound according to claim 6, wherein s is zero or one and T is chloro, fluoro, or trifluoromethyl.

8. A compound according to claim 5, wherein $Z_3$ is oxa.

9. A compound according to claim 8, wherein s is zero or one and T is chloro, fluoro, or trifluoromethyl.

10. A compound according to claim 4, wherein Y is cis-CH=CH—.

11. A compound according to claim 10, wherein $Z_3$ is methylene.

12. A compound according to claim 11, wherein s is zero or one and T is chloro, fluoro, or trifluoromethyl.

13. A compound according to claim 10, wherein $Z_3$ is oxa.

14. A compound according to claim 13, wherein s is zero or one, and T is chloro, fluoro, or trifluoromethyl.

15. A compound according to claim 4, wherein Y is trans-CH=CH—.

16. A compound according to claim 15, wherein $Z_3$ is methylene.

17. A compound according to claim 16, wherein s is zero or one and T is chloro, fluoro, or trifluormethyl.

18. A compound according to claim 17, wherein $Z_1$ is cis-CH=CH—$CH_2$—$(CH_2)_g$—$CF_2$—, cis-CH=CH—$CH_2$—$(CH_2)_g$—$CH_2$—, or cis-$CH_2$—CH=CH—$(CH_2)_g$—$CH_2$—.

19. A compound according to claim 18, wherein g is 1.

20. A compound according to claim 19, wherein $R_5$ and $R_6$ are both hydrogen.

21. A compound according to claim 20, wherein $R_3$ and $R_4$ are both hydrogen.

22. 17-Phenyl-18,19,20-trinor-$PGD_2$, a compound according to claim 21.

23. 2,2-Difluoro-17-phenyl-18,19,20-trinor-$PGD_2$, a compound according to claim 21.

24. cis-4,5-Didehydro-17-phenyl-18,19,20-trinor-$PGD_2$, a compound according to claim 21.

25. A compound according to claim 20, wherein $R_3$ and $R_4$ are both fluoro.

26. 16,16-Difluoro-17-phenyl-18,19,20-trinor-$PGD_2$, a compound according to claim 25.

27. A compound according to claim 17, wherein $Z_1$ is —$(CH_2)_3$—$(CH_2)_g$—$CF_2$— or —$(CH_2)_3$—$(CH_2)_g$—$CH_2$—.

28. A compound according to claim 27, wherein g is 1.

29. A compound according to claim 28, wherein $R_5$ and $R_6$ are both hydrogen.

30. A compound according to claim 29, wherein $R_3$ and $R_4$ are both hydrogen.

31. 17-Phenyl-18,19,20-trinor-$PGD_1$, a compound according to claim 30.

32. A compound according to claim 17, wherein $Z_1$ is —$CH_2$—O—$CH_2$—$(CH_2)_g$—$CH_2$—, —$(CH_2)_2$—O—$(CH_2)_g$—$CH_2$—, or —$(CH_2)_3$—O—$(CH_2)_g$—.

33. A compound according to claim 32, wherein g is 1.

34. A compound according to claim 33, wherein $R_5$ and $R_6$ are both hydrogen.

35. A compound according to claim 34, wherein $R_3$ and $R_4$ are both hydrogen.

36. 5-Oxa-17-phenyl-18,19,20-trinor-$PGD_1$, a compound according to claim 35.

37. A compound according to claim 17, wherein $Z_1$ is

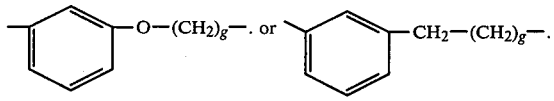

38. A compound according to claim 37, wherein g is 1.

39. A compound according to claim 38, wherein $R_5$ and $R_6$ are both hydrogen.

40. A compound according to claim 39, wherein $R_3$ and $R_4$ are both hydrogen.

41. 3,7-Inter-m-phenylene-4,5,6-trinor-$PGD_1$, a compound according to claim 40.

42. A compound according to claim 15, wherein $Z_3$ is oxa.

43. A compound according to claim 42, wherein s is 0 or 1 and T is chloro, fluoro, or trifluoromethyl.

44. A compound according to claim 43, wherein $Z_1$ is cis-CH=CH—$CH_2$—$(CH_2)_g$—$CF_2$—.

45. A compound according to claim 44, wherein g is 1.

46. A compound according to claim 45, wherein $R_5$ and $R_6$ are both hydrogen.

47. A compound according to claim 46, wherein $R_3$ and $R_4$ are both hydrogen.

48. 2,2-Difluoro-16-phenoxy-17,18,19,20-tetranor-$PGD_2$, a compound according to claim 47.

49. A compound according to claim 43, wherein $Z_1$ is cis-CH=CH—$CH_2$—$(CH_2)_g$—$CH_2$—.

50. A compound according to claim 49, wherein g is 3.

51. A compound according to claim 50, wherein $R_5$ and $R_6$ are both hydrogen.

52. A compound according to claim 51, wherein $R_3$ and $R_4$ are both hydrogen.

53. 2a,2b-Dihomo-16-phenoxy-17,18,19,20-tetranor-$PGD_2$, a compound according to claim 52.

54. A compound according to claim 51, wherein $R_3$ and $R_4$ are both methyl.

55. 16-Methyl-16-phenoxy-18,19,20-trinor-$PGD_2$, a compound according to claim 54.

56. A compound according to claim 43, wherein $Z_1$ is cis-$CH_2$—$CH=CH$—$(CH_2)_g$—$CH_2$—.

57. A compound according to claim 56, wherein g is 1.

58. A compound according to claim 57, wherein $R_5$ and $R_6$ are both hydrogen.

59. A compound according to claim 58, wherein $R_3$ and $R_4$ are both hydrogen.

60. cis-4,5-Didehydro-16-phenoxy-17,18,19,20-tetranor-$PGD_2$, a compound according to claim 59.

61. A compound according to claim 58, wherein $R_3$ and $R_4$ are both.

62. cis-4,5-Didehydro-16-methyl-16-phenoxy-18,19,20-trinor-$PGD_1$, a compound according to claim 61.

63. A compound according to claim 43, wherein $Z_1$ is —$(CH_2)_3$—$(CH_2)_g$—$CF_2$—.

64. A compound according to claim 63, wherein g is 1.

65. A compound according to claim 64, wherein $R_5$ and $R_6$ are both hydrogen.

66. A compound according to claim 65, wherein $R_3$ and $R_4$ are both hydrogen.

67. 2,2-Difluoro-16-phenoxy-17,18,19,20-tetranor-$PGD_1$, a compound according to claim 66.

68. A compound according to claim 65, wherein $R_3$ and $R_4$ are both fluoro.

69. 2,2,16,16-Tetrafluoro-16-phenoxy-17,18,19,20-tetranor-$PGD_1$, a compound according to claim 68.

70. A compound according to claim 43, wherein $Z_1$ is —$(CH_2)_3$—$(CH_2)_g$—$CH_2$—.

71. A compound according to claim 70, wherein g is 3.

72. A compound according to claim 71, wherein $R_5$ and $R_6$ are both hydrogen.

73. A compound according to claim 72, wherein $R_3$ and $R_4$ are both hydrogen.

74. 16-Phenoxy-17,18,19,20-tetranor-$PGD_1$, a compound according to claim 73.

75. A compound according to claim 72, wherein $R_3$ and $R_4$ are both fluoro.

76. 16,16-Difluoro-16-phenoxy-17,18,19,20-tetranor-$PGD_1$, a compound according to claim 75.

77. A compound according to claim 43, wherein $Z_1$ is —$CH_2$—O—$CH_2$—$(CH_2)_g$—$CH_2$—, —$(CH_2)_2$—O—$CH_2$—$(CH_2)_g$—$CH_2$—, or —$(CH_2)_3$—O—$(CH_2)_g$—.

78. A compound according to claim 77, wherein g is 1.

79. A compound according to claim 78, wherein $R_3$, $R_4$, $R_5$, and $R_6$ are all hydrogen.

80. 5-Oxa-16-phenoxy-17,18,19,20-tetranor-$PGD_1$, a compound according to claim 79.

81. A compound according to claim 43, wherein $Z_1$

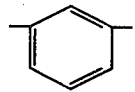—O—$(CH_2)_g$—, or 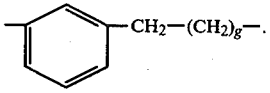—$CH_2$—$(CH_2)_g$—.

82. A compound according to claim 81, wherein g is 1 and $R_3$, $R_4$, $R_5$, and $R_6$ are all hydrogen.

83. A compound according to claim 1, wherein D is

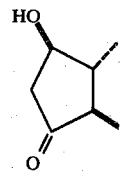

84. A compound according to claim 1, wherein D is

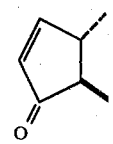

85. A compound according to claim 84, wherein $M_1$ is

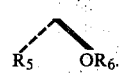

86. A compound according to claim 84, wherein $M_1$ is

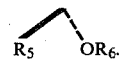

87. A compound according to claim 86, wherein Y is cis-$CH=CH$—.

88. A compound according to claim 87, wherein $Z_3$ is methylene.

89. A compound according to claim 88, wherein s is 0 or 1 and T is chloro, fluoro or trifluoromethyl.

90. A compound according to claim 87, wherein $Z_3$ is oxa.

91. A compound according to claim 90, wherein s is 0 or 1 and T is chloro, fluoro, or trifluoromethyl.

92. A compound according to claim 86, wherein Y is trans-$CH=CH$—.

93. A compound according to claim 92, wherein $Z_3$ is methylene.

94. A compound according to claim 93, wherein s is 0 or 1 and T is chloro, fluoro, or trifluoromethyl.

95. A compound according to claim 94, wherein $Z_1$ is cis-$CH=CH$—$CH_2$—$(CH_2)_g$—$CF_2$—, cis-$CH=CH$—$CH_2$—$(CH_2)_g$—$CH_2$—, or cis-$CH_2$—$CH=CH$—$(CH_2)_g$—$CH_2$—.

96. A compound according to claim 95, wherein g is 1.

97. A compound according to claim 96, wherein $R_5$ and $R_6$ are both hydrogen.

98. A compound according to claim 97, wherein $R_3$ and $R_4$ are both hydrogen.

99. 2,2-Difluoro-17-phenyl-18,19,20-trinor-9-deoxy-9,10-didehydro-$PGD_2$, a compound according to claim 98.

100. 17-Phenyl-18,19,20-trinor-9-deoxy-9,10-didehydro-$PGD_2$, a compound according to claim 98.

101. cis-4,5-Didehydro-17-phenyl-18,19,20-trinor-9-deoxy-9,10-didehydro-$PGD_1$, a compound according to claim 98.

102. A compound according to claim 94, wherein $Z_1$ is —$(CH_2)_3$—$(CH_2)_g$—$CF_2$— or —$(CH_2)_3$—$(CH_2)_g$—$CH_2$—.

103. A compound according to claim 102, wherein g is 1.

104. A compound according to claim 103, wherein $R_5$ and $R_6$ are both hydrogen.

105. A compound according to claim 104, wherein $R_3$ and $R_4$ are both hydrogen.

106. 2,2-Difluoro-17-phenyl-18,19,20-trinor-9-deoxy-9,10-didehydro-PGD$_1$, a compound according to claim 105.

107. 17-phenyl-18,19,20-trinor-9-deoxy-9,10-didehydro-PGD$_1$, a compound according to claim 105.

108. A compound according to claim 94, wherein $Z_1$ is —$CH_2$—O—$CH_2$—$(CH_2)_g$—$CH_2$—, —$(CH_2)_2$—O—$CH_2$—$(CH_2)_g$—$CH_2$—, or —$(CH_2)_3$—O—$(CH_2)_g$—.

109. A compound according to claim 108, wherein g is 1.

110. A compound according to claim 109, wherein $R_5$ and $R_6$ are both hydrogen.

111. A compound according to claim 110, wherein $R_3$ and $R_4$ are both hydrogen.

112. 5-Oxa-17-phenyl-18,19,20-trinor-9-deoxy-9,10-didehydro-PGD$_1$, a compound according to claim 111.

113. A compound according to claim 94, wherein $Z_1$ is

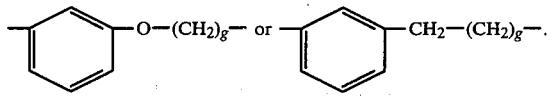

114. A compound according to claim 113, wherein g is 1.

115. A compound according to claim 114, wherein $R_5$ and $R_6$ are both hydrogen.

116. A compound according to claim 115, wherein $R_3$ and $R_4$ are both hydrogen.

117. 3,7-Inter-m-phenylene-4,5,6-trinor-17-phenyl-18,19,20-trinor-PGD$_1$, a compound according to claim 116.

118. A compound according to claim 92, wherein $Z_3$ is oxa.

119. A compound according to claim 118, wherein s is 0 or 1 and T is chloro, fluoro, or trifluoromethyl.

120. A compound according to claim 119, wherein $Z_1$ is cis-CH=CH—$CH_2$—$(CH_2)_g$—$CF_2$—, cis-CH=CH—$CH_2$—$(CH_2)_g$—$CH_2$—, or cis-$CH_2$—CH=CH—$(CH_2)_g$—$CH_2$—.

121. A compound according to claim 120, wherein g is 1.

122. A compound according to claim 121, wherein $R_5$ and $R_6$ are both hydrogen.

123. A compound according to claim 122, wherein $R_3$ and $R_4$ are both hydrogen.

124. 2,2-Difluoro-16-phenoxy-17,18,19,20-tetranor-9-deoxy-9,10-didehydro-PGD$_2$, a compound according to claim 123.

125. 16-Phenoxy-17,18,19,20-tetranor-9-deoxy-9,10-didehydro-PGD$_2$, a compound according to claim 123.

126. cis-4,5-Didehydro-16-phenoxy-17,18,19,20-tetranor-9-deoxy-9,10-didehydro-PGD$_1$, a compound according to claim 123.

127. A compound according to claim 119, wherein $Z_1$ is —$(CH_2)_3$—$(CH_2)_g$—$CF_2$— or —$(CH_2)_3$—$(CH_2)_g$—$CH_2$—.

128. A compound according to claim 127, wherein g is 1.

129. A compound according to claim 128, wherein $R_5$ and $R_6$ are both hydrogen.

130. A compound according to claim 129, wherein $R_3$ and $R_4$ are both hydrogen.

131. 2,2-Difluoro-16-phenoxy-17,18,19,20-tetranor-9-deoxy-9,10-didehydro-PGD$_1$, a compound according to claim 130.

132. 16-Phenoxy-17,18,19,20-tetranor-9-deoxy-9,10-didehydro-PGD$_1$, a compound according to claim 130.

133. A compound according to claim 119, wherein $Z_1$ is —$CH_2$—O—$CH_2$—$(CH_2)_g$—$CH_2$—, —$(CH_2)_2$—O—$CH_2$—$(CH_2)_g$—$CH_2$—, or —$(CH_2)_3$—O—$(CH_2)_g$—.

134. A compound according to claim 133, wherein g is 1.

135. A compound according to claim 134, wherein $R_5$ and $R_6$ are both hydrogen.

136. A compound according to claim 135, wherein $R_3$ and $R_4$ are both hydrogen.

137. 5-Oxa-16-phenoxy-17,18,19,20-tetranor-9-deoxy-9,10-didehydro-PGD$_1$, a compound according to claim 136.

138. A compound according to claim 119, wherein $Z_1$ is

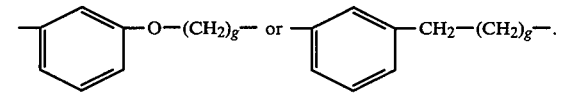

139. A compound according to claim 138, wherein g is 1.

140. A compound according to claim 139, wherein $R_5$ and $R_6$ are both hydrogen.

141. A compound according to claim 140, wherein $R_3$ and $R_4$ are both hydrogen.

142. 3,7-Inter-m-phenylene-16-phenoxy-17,18,19,20-tetranor-9-deoxy-9,10-didehydro-PGD$_1$, a compound according to claim 141.

* * * * *

UNITED STATES PATENT OFFICE
CERTIFICATE OF CORRECTION

Patent No. 4,365,075            Dated 21 December 1982

Inventor(s) Douglas R. Morton, Jr.

It is certified that error appears in the above-identified patent and that said Letters Patent are hereby corrected as shown below:

Column 1, lines 15-18, that portion of the formula should appear as follows:

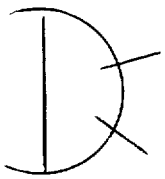

Signed and Sealed this

Eighteenth Day of December 1984

[SEAL]

Attest:

Attesting Officer

GERALD J. MOSSINGHOFF

Commissioner of Patents and Trademarks